United States Patent
Cunningham

(10) Patent No.: US 12,239,755 B2
(45) Date of Patent: Mar. 4, 2025

(54) METHOD, DEVICE, AND SYSTEM FOR DISINFECTION

(71) Applicant: NEVOA LIFE SCIENCES, Gilbert, AZ (US)

(72) Inventor: Emmett Manuel Cunningham, Glen Allen, VA (US)

(73) Assignee: NEVOA LIFE SCIENCES, Gilbert, AZ (US)

( * ) Notice: Subject to any disclaimer, the term of this patent is extended or adjusted under 35 U.S.C. 154(b) by 854 days.

(21) Appl. No.: 17/446,753

(22) Filed: Sep. 2, 2021

(65) Prior Publication Data

US 2021/0393833 A1 Dec. 23, 2021

Related U.S. Application Data

(63) Continuation of application No. 16/231,480, filed on Dec. 22, 2018, now Pat. No. 11,135,328, which is a
(Continued)

(51) Int. Cl.
*A61L 2/22* (2006.01)
*A01N 25/06* (2006.01)
(Continued)

(52) U.S. Cl.
CPC ............ *A61L 2/22* (2013.01); *A01N 25/06* (2013.01); *A61L 9/14* (2013.01); *B05B 3/02* (2013.01);
(Continued)

(58) Field of Classification Search
CPC ..... A61L 2/22; A61L 9/14; B05B 3/02; B05B 5/025
See application file for complete search history.

(56) References Cited

U.S. PATENT DOCUMENTS 2,352,527 A 6/1944 Favor
3,026,966 A 3/1962 Asklof
(Continued)

FOREIGN PATENT DOCUMENTS

EP 1129762 9/2001
EP 1129762 A1 9/2001
(Continued)

OTHER PUBLICATIONS

EP Search Report & Written Opinion for EP Application No. 15 73 5140, dated Jul. 5, 2017, 11 pages.
(Continued)

*Primary Examiner* — Sean E Conley
(74) *Attorney, Agent, or Firm* — Hoffman Warnick LLC

(57) ABSTRACT

Embodiments of the invention relate generally to disinfection and, more particularly, to methods, devices, and systems for disinfection of a space. In one embodiment, the invention provides a disinfecting system comprising: a disinfecting composition; and a device for producing a fog of the disinfecting composition, the fog comprising liquid droplets having diameters between about 0.5 micron and about 20 microns. In some embodiments, the invention includes a dehumidifying device for removing the fog of the disinfecting composition from the space.

18 Claims, 1 Drawing Sheet

Related U.S. Application Data continuation of application No. 15/108,745, filed as application No. PCT/US2015/010447 on Jan. 7, 2015, now Pat. No. 10,188,764.

(60) Provisional application No. 61/924,980, filed on Jan. 8, 2014.

(51) Int. Cl.

| | | |
|---|---|---|
| *A61L 9/14* | (2006.01) | |
| *B05B 3/02* | (2006.01) | |
| *B05B 5/025* | (2006.01) | |
| *B05B 7/08* | (2006.01) | |
| *B05B 17/06* | (2006.01) | |
| *A61L 9/16* | (2006.01) | |
| *B05B 1/26* | (2006.01) | |
| *B05B 3/10* | (2006.01) | |
| *B05B 7/00* | (2006.01) | |

(52) U.S. Cl.
CPC ............... B05B 5/025 (2013.01); B05B 7/08 (2013.01); *A61L 9/16* (2013.01); *A61L 2202/15* (2013.01); *A61L 2202/25* (2013.01); *A61L 2209/132* (2013.01); *A61L 2209/135* (2013.01); *A61L 2209/14* (2013.01); *B05B 1/26* (2013.01); *B05B 3/10* (2013.01); *B05B 7/0012* (2013.01); *B05B 17/0669* (2013.01)

(56) References Cited

U.S. PATENT DOCUMENTS

| | | | |
|---|---|---|---|
| 3,474,598 A | 10/1969 | Keuls | |
| 4,540,124 A * | 9/1985 | Haruch | ................ B05B 3/1064 |
| | | | 239/223 |
| 6,832,753 B1 | 12/2004 | Huang | |
| 8,382,008 B1 | 2/2013 | Ricciardi et al. | |
| 8,529,833 B2 * | 9/2013 | Morgantini | ............... A61L 2/22 |
| | | | 239/700 |
| 10,188,764 B2 * | 1/2019 | Cunningham | ......... A01N 25/06 |
| 2008/0156320 A1 | 7/2008 | Low et al. | |
| 2008/0292498 A1 | 11/2008 | Resch et al. | |
| 2011/0091354 A1 | 4/2011 | Schwartz et al. | |
| 2011/0123394 A1 * | 5/2011 | Plantinga | .................. A61L 2/22 |
| | | | 422/292 |
| 2011/0236490 A1 | 9/2011 | Cunningham | |
| 2017/0097163 A1 | 4/2017 | Law et al. | |
| 2017/0138622 A1 | 5/2017 | Wang et al. | |

FOREIGN PATENT DOCUMENTS

| | | |
|---|---|---|
| JP | 2014074571 A | 4/2014 |
| WO | 2010/128480 | 11/2010 |
| WO | 2010128480 A2 | 11/2010 |
| WO | 2012032338 A1 | 3/2012 |
| WO | 2013090540 | 6/2013 |
| WO | 2013090540 A1 | 6/2013 |

OTHER PUBLICATIONS

International Search Report and Written Opinion PCT/US2015/105852 dated Apr. 7, 2015 9 pages.
International Search Report and Written Opinion PCT/US15/10447, dated Apr. 7, 2015, 9 pages.
EP Search Report & Written Opinion for EP Application No. 15735140.4, dated Jul. 5, 2017, 11 pages.

* cited by examiner

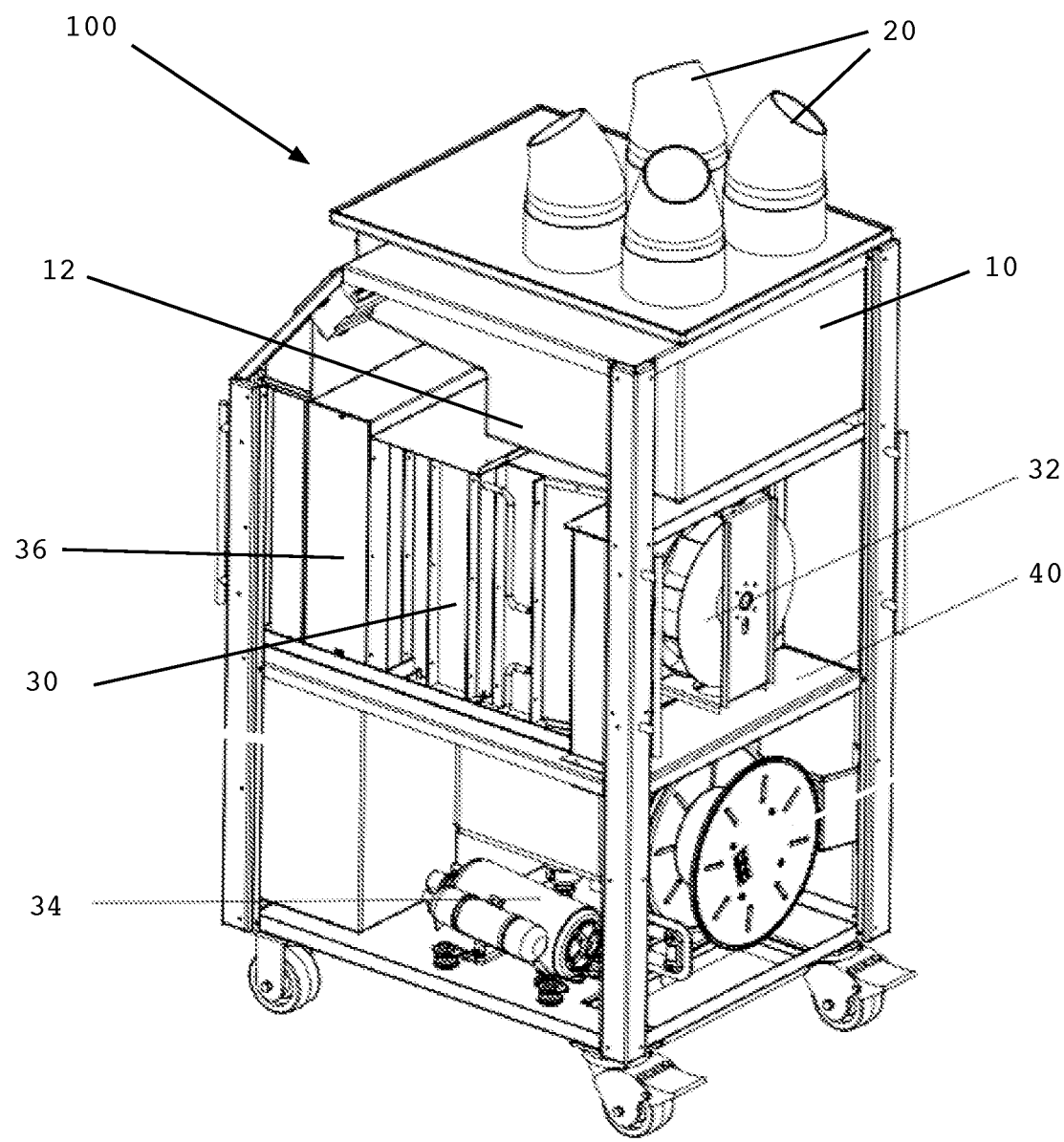

METHOD, DEVICE, AND SYSTEM FOR DISINFECTION

CROSS-REFERENCE TO RELATED APPLICATIONS

This application claims the benefit of U.S. patent application Ser. No. 16/231,480, filed 22 Dec. 2018, which claims the benefit of U.S. patent application Ser. No. 15/108,745, filed 28 Jun. 2016, now U.S. Pat. No. 10,188,764, which is the U.S. national phase of PCT Patent Application Serial No. PCT/US2015/010447, filed 7 Jan. 2015, which in turn claims priority to U.S. Provisional Patent Application Ser. No. 61/924,980, filed 8 Jan. 2014, each of which is hereby incorporated herein.

BACKGROUND

Embodiments of the invention relate generally to disinfection and, more particularly, to methods, devices, and systems for disinfection of an enclosed space.

Infectious agents, including fungi, bacteria, and viruses, may be found in many areas frequented or inhabited by humans and animals. Within such areas, such infections agents may be transmitted to humans and animals through contact with the area's surfaces and/or inhalation of airborne agents within the area's atmosphere. Such areas include, without limitation, classrooms, gymnasiums and locker rooms, airplane cabins, cruise ships, veterinary clinics, hospitals, including hospital operating rooms, nursing homes, daycare centers, public restrooms, subway cars, and train cars.

An effective method of disinfecting both the atmosphere and the surfaces—horizontal, vertical, and obscured—within such spaces may significantly reduce the instances of infection by these agents.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 1 shows a disinfecting apparatus according to one embodiment of the invention.

It is noted that the drawings of the invention are not to scale. The drawings are intended to depict only typical aspects of the invention, and therefore should not be considered as limiting the scope of the invention.

SUMMARY OF EMBODIMENTS OF THE INVENTION

In one embodiment, the invention provides a method of disinfecting an area or enclosed space, the method comprising: introducing into the area or enclosed space a fog of a disinfecting composition comprising liquid droplets having diameters between about 0.5 micron and about 20 micron, the disinfecting composition comprising at least one of the following: hypochlorous acid, hypochlorite ion, sodium hypochlorite, chlorine, silver, hydrogen peroxide, ethaneperoxoic acid, tetraacetylethylenediamine, caprylic acid, alkyl dimethyl benzyl ammonium chloride, didecyl dimethyl ammonium chloride, triethylene glycol, peroxyacetic acid, isopropyl alcohol, octanaminium, octyl decyl dimethyl ammonium chloride, benzyl-p-chlorophenol, phenylphenol, dimethyl benzyl ammonium saccharinate, sodium dichloroisocyanurate dehydrate, or sodium chlorite.

In another embodiment, the invention provides an apparatus for disinfecting an area or enclosed space, the apparatus comprising: a device for producing a fog comprising liquid droplets having diameters between about 0.5 micron and about 20 microns; and at least one port for discharging the fog into the area or enclosed space.

In still another embodiment, the invention provides a disinfecting system comprising: a disinfecting composition; and a device for producing a fog of the disinfecting composition, the fog comprising liquid droplets having diameters between about 0.5 micron and about 20 microns.

In still yet another embodiment, the invention provides a dehumidifying system comprising: a dehumidifying device including at least one moisture filtering apparatus; and at least one additional moisture filtering apparatus configured upstream of the dehumidifying device. In some embodiments of the invention, the at least one moisture filtering apparatus, the at least one additional moisture filtering apparatus, or both, may include or comprise a low-moisture droplet mesh screen.

DETAILED DESCRIPTION

Methods according to various embodiments of the invention include the use of a high-density fogging delivery system to produce a high-density fog of a disinfecting composition which is then distributed within an area, such as an enclosed space, to provide disinfection of infections agents. The disinfecting composition, according to some embodiments of the invention, includes hypochlorous acid and hypochlorite ion. In other embodiments of the invention, the disinfecting composition includes one or more of sodium hypochlorite, chlorine, silver, or hydrogen peroxide. In still other embodiments, the disinfecting composition may additionally or instead include one or more of ethaneperoxoic acid, tetraacetylethylenediamine, caprylic acid, alkyl dimethyl benzyl ammonium chloride, didecyl dimethyl ammonium chloride, triethylene glycol, peroxyacetic acid, isopropyl alcohol, octanaminium, octyl decyl dimethyl ammonium chloride, benzyl-p-chlorophenol, phenylphenol, dimethyl benzyl ammonium saccharinate, sodium dichloroisocyanurate dehydrate, or sodium chlorite. The disinfecting composition may be provided as a pre-manufactured liquid or prepared from separate components within the delivery system itself.

Disinfecting compositions such as hypochlorous acid and hypochlorite ion have been found to be highly effective against virtually all fungi, bacteria, and viruses while also showing no adverse effect on the cornea, sclera, mucous membrane, oropharynx/uvula area, epidermis, dermis, or fatty tissues of humans or animals after extended contact.

For example, a high-density fogging delivery system according to one embodiment of the invention may include a piezo ultrasonic disc nebulizer or similar device capable of producing a fog of the disinfecting composition comprising liquid droplets between about 0.5 micron and 20 microns in diameter, e.g., between about 0.5 micron and about 3 microns in diameter.

Such nebulizers typically function from a fixed position in the base of a storage tank or receptacle, where a vibrational energy—generated from a supplied voltage—is transmitted in a direction perpendicular to the resonant surface of the piezo resonator.

It has been discovered that the distance between the surface of the piezo resonator and the surface of the liquid in the storage tank has a major effect on atomization efficiency. Thus, according to some embodiments of the invention, the piezo nebulizer or similar device is disposed in an atomizing tray, where the depth of the disinfecting composition—and therefore the distance between the piezo resonator and the surface of the disinfecting composition—may be substantially maintained through use, for example, of a recirculating pump or similar apparatus even as the disinfecting composition is atomized and discharged.

It has also been found that the frequency of oscillation of the piezo resonator has a significant effect on the efficiency of disinfection using systems and devices according to the invention. Frequencies between about 1.50 MHz and about 2.50 MHz, and even more preferably between about 1.65 MHz and about 2.10 MHz, produce a fog of droplets having optimal diameters for efficient dispersal without saturating the area to be disinfected. Lower frequencies produce droplets that are too large and which "drop out" of the air stream. Higher frequencies produce droplets that are too small and which tend to "float" or remain suspended in the air stream without contacting the surfaces sought to be disinfected.

One skilled in the art will recognized that fogs of disinfecting compositions may be produced by other methods as well. Such methods include, for example, small orifice misting nozzles, which pass a fluid through a small orifice at high velocity, where the resulting shearing forces break the fluid into fine droplets.

Impingement misting nozzles may also be employed. These devices force the fluid onto a pin or similar structure just outside the exit orifice, which again breaks the fluid into very fine droplets. These nozzles may employ a larger orifice, as compared to those in the small orifice misting nozzles, which may be beneficial when utilizing disinfecting compositions with higher viscosities and/or suspensions.

Air atomizing nozzles may also be employed in embodiments of the invention. These pneumatic nozzles use compressed air to break apart the fluid, allowing for very fine atomization, even at low pressures.

Once produced, regardless of the method, a fog of disinfectant composition may be discharged from the delivery system through one or more ports or tubes using a fan. The fog may then be permitted to expand throughout the area or enclosed space, thereby disinfecting both its atmosphere and its surfaces, including obscured or recessed surfaces that would otherwise be difficult or impossible to disinfect.

Fogs of a disinfecting composition having different particle sizes may be produced using other fogging devices. For example, using a single or multi-head spray nozzle, a disinfecting fog having droplets between about 3 microns and about 20 microns, e.g., between about 3 microns and about 5 microns, may be produced. Using a single or multi-head high-speed rotary disc nebulizer will produce a fog having droplets between about 2 microns and about 20 microns, e.g., between about 2 microns and about 5 microns.

Employing disinfecting fogs comprised of liquid droplets in size ranges such as these provide at least two clear advantages over other disinfecting methods and systems. First, the small droplet size permits the disinfecting fog to reach into small recesses, including minute cracks or grains in surfaces that otherwise cannot be reached. Second, the small droplet size improves the extent of disinfection, regardless of the size of the infectious agent. For example, disinfecting fogs comprising droplets of this size have been shown to kill virtually all fungi, bacteria, and viruses, including methicillin-resistant *Staphylococcus aureus* (MRSA) and *Clostridium difficile*.

The pH of the disinfecting composition is also important in achieving effective disinfection. Disinfecting compositions having a pH between about 3 and about 7.5, e.g., between about 5 and about 7.5, e.g., between about 5 and about 7, e.g., between about 6 and about 7, have been found to be particularly effective.

In still other embodiments of the invention, an electrical charge may be induced in or imparted to the disinfecting fog. For example, an electrostatic aerosol applicator may be employed to produce a negatively charged disinfecting fog by passing the fog across or adjacent an induction electrode, which induces a charge in each droplet. Positively charged surfaces in the area or enclosed space will attract the negatively charged droplets, causing the droplets to adhere, even, for example, on downwardly-facing horizontal surfaces, which otherwise would be less likely than upwardly-facing horizontal surfaces to come in contact with uncharged droplets. In fact, it has been found that the electrical attraction of such negatively-charged droplets is approximately 40 times stronger than is the force of gravity on such droplets.

In addition, the induction of a charge on the droplets of the disinfecting fog reduces the rate and extent of agglomeration among the droplets. This has the effect of improving distribution of the disinfecting fog within the area or enclosed space.

In still other embodiments of the invention, a disinfecting system may include a moisture-eliminating device or apparatus. This provides a number of advantages, including the reduction of moisture which otherwise may harbor or promote the growth of molds.

For example, after distributing a disinfecting fog within an area or enclosed space, a low-micron moisture droplet filter or a low-micron moisture droplet air-flow vane may be used to remove up to about 99% of the volume of disinfecting composition initially introduced to the area or enclosed space. In doing so, the filter traps both the disinfecting composition and any infectious agents on its surfaces, thereby providing a secondary field for disinfection. Dehumidifying the atmosphere of the area or enclosed space prior to introduction of the disinfecting fog has also been found to improve the disinfecting capabilities of the methods, devices, and systems of the invention.

Some embodiments of the invention employ an in-line dehumidifier, i.e., a dehumidifier incorporated into the same device that introduces the disinfecting composition into the area or enclosed space. An in-line dehumidifier has been found to more quickly and efficiently remove the disinfecting composition than can an external dehumidifier of the same or larger dehumidifying capacity.

For example, a disinfecting device according to one embodiment of the invention that does not include a dehumidifying device was employed to disperse a total of 2.5 L of a disinfecting solution into a sealed space at a rate of 180-200 mL per minute. The sealed space was fogged to "white out" in 14 minutes. An external dehumidifying unit (a Phoenix R200 LGR dehumidifier) was then used in conjunction with four external circulating fans to clear the room in 22 minutes.

A device according to another embodiment of the invention that included an in-line dehumidifying device was employed to disperse 2.5 L of the same disinfecting solution into a sealed space of the same size at the same rate of 180-200 mL per minute. Once fogged to "white out" in the same 14 minutes, the in-line dehumidifying device was employed and cleared the room in seven minutes, a 48% improvement over the use of the external dehumidifier and circulating fans.

More specifically, the in-line dehumidifier was outfitted with a low-micron moisture droplet mesh screen upstream of the dehumidifier and another within the dehumidifier itself. The upstream "pre-dehumidifier" screen was able to remove 500 mL of liquid ahead of the dehumidifier, with the dehumidifier itself then removing another 1000 mL. This upstream dehumidification allowed for more efficient functioning of the dehumidifier, permitting faster clearing of the room.

Such low-moisture droplet mesh screens capture larger (about 3 micron diameter and larger) droplets differently than smaller (less than about 3 micron diameter) droplets. The larger droplets have sufficient momentum to "break" from the air stream in which they are carried and inertia will carry them in a straight line if the air stream turns, so that these larger droplets carry on and impact a filter surface. These larger droplets are collected more efficiently at higher velocities.

The smaller droplets typically do not have sufficient mass to "break" from the air stream and are instead captured by filter fibers by direct contact.

Very small (submicron) droplets, on the other hand, while also not having sufficient momentum to break from the air stream, exhibit random (Brownian) movement within the air stream. Such very small droplets are also collected by direct contact with filter fibers and are retained by such fibers by van der Waals forces. However, these very small droplets are more efficiently collected at lower air stream velocities, which increases the likelihood that a very small droplet will contact a filter fiber, even where the space between the fibers is greater than the diameters of the droplets.

Accordingly, a dehumidification system according to embodiments of the invention that includes a plurality of air flow velocities, as may be achieved, for example, by altering the volume through which the air stream flows, may be more effective in removing both larger and very small droplets than would a system that substantially maintains a single air flow velocity.

In other embodiments of the invention, dehumidifying devices according to the invention may include filters having low-micron moisture droplet air-flow vanes. These filters may include those that employ an impingement-type separator. These have curved passages through which the humidified air passes. The mass of the disinfectant droplets being greater than that of the air in which they are contained results in their impact with the surfaces of the curved passages. These droplets, after impacting the passage surfaces, form a liquid film that coalesces into larger droplets that are gravitationally discharged from the filter. As such, according to some embodiments of the invention, a condensation tank or similar device may be provided for storage of liquids accumulated as a consequence of the dehumidification process.

In some embodiments of the invention, dehumidification of the atmosphere of an area or enclosed space is achieved through the intake of non-dehumidified air through multiple intakes of a disinfecting device and/or the discharge of dehumidified air through multiple other ports of the device. Having multiple intake and discharge points creates air turbulence in the area or enclosed space, further enhancing the dehumidifying process.

In still other embodiments of the invention, a carbon filter or similar device may be employed to capture any chlorine or chloride gas during or separate from such dehumidification, which may serve to reduce or eliminate undesirable odors from the dehumidified air. A gram of activated carbon may have a surface area between 500 m$^2$ and 1500 m$^2$, and a pound of activated carbon will adsorb about one sixth of its weight in chlorine compounds alone, while also removing volatile organic compounds (VOCs), etc.

FIG. 1 shows a perspective view of an apparatus 100 according to one embodiment of the invention. Apparatus 100 includes a tank 10 for containing a disinfecting composition. Tank 10 includes a base 12 to which one or more nebulizers or similar devices (not shown) may be affixed or secured.

Once a fog of disinfecting composition is produced, such as described above, the fog may be discharged through one or more ports or tubes 20, which, as shown in FIG. 1 may be angled with respect to vertical and/or horizontal axes of apparatus 100. Such discharge may be achieved using, for example, a fan or similar device (not shown).

Apparatus 100 further includes a dehumidifying device 30 having a dehumidifier fan 32 and a dehumidifier compressor 34, as well as a filtering device 40, such as an activated carbon filter. As noted above, apparatus 100 may further include one or more moisture droplet eliminator filters 36 or similar devices, which may be disposed to receive incoming air upstream of the dehumidifying device.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for disinfecting an area or enclosed space, the apparatus comprising:
    an atomizing tray;
    an atomizing device within the atomizing tray, the atomizing device being operable to produce a fog comprising liquid droplets having diameters between about 0.5 micron and about 20 microns;
    a tank for holding a quantity of a disinfecting composition;
    a recirculating pump for transferring the disinfecting composition from the tank to the atomizing tray and maintaining a depth of the disinfecting composition within the atomizing tray;
    at least one port for discharging the fog into the area or enclosed space; and
    an in-line dehumidifying device.

2. The apparatus of claim 1, wherein the atomizing device for producing the fog includes a piezo disc nebulizer operable at a frequency between about 1.50 MHz and about 2.50 MHz.

3. The apparatus of claim 1, wherein the atomizing device for producing the fog includes a high-speed rotary disc atomizer.

4. The apparatus of claim 1, wherein the atomizing device for producing the fog includes at least one device selected from a group consisting of: small orifice misting nozzles, impingement misting nozzles, and air atomizing nozzles.

5. The apparatus of claim 1, further comprising:
a device for inducing an electrical charge in at least a portion of the liquid droplets.

6. The apparatus of claim 1, further comprising:
a filtering device for removing odor from an atmosphere.

7. The apparatus of claim 6, wherein the filtering device includes activated carbon.

8. A disinfecting system comprising:
a tank containing a quantity of a disinfecting composition; and
an atomizing tray;
a recirculating pump for transferring the disinfecting composition from the tank to the atomizing tray and maintaining a depth of the disinfecting composition within the atomizing tray;
an atomizing device within the atomizing tray, the atomizing device being operable to produce a fog of the disinfecting composition, the fog comprising liquid droplets having diameters between about 0.5 micron and about 20 microns, and the device comprising:
a high-speed rotary disc atomizer;
at least one port for discharging the fog into the area or enclosed space; and
an in-line dehumidifying device.

9. The disinfecting system of claim 8, wherein the disinfecting composition includes at least one of the following: hypochlorous acid, hypochlorite ion, sodium hypochlorite, chlorine, silver, hydrogen peroxide, ethaneperoxoic acid, tetraacetylethylenediamine, caprylic acid, alkyl dimethyl benzyl ammonium chloride, didecyl dimethyl ammonium chloride, triethylene glycol, peroxyacetic acid, isopropyl alcohol, octanaminium, octyl decyl dimethyl ammonium chloride, benzyl-p-chlorophenol, phenylphenol, dimethyl benzyl ammonium saccharinate, sodium dichloroisocyanurate dehydrate, or sodium chlorite.

10. The disinfecting system of claim 8, wherein the disinfecting composition comprises hypochlorous acid and hypochlorite ion.

11. The disinfecting system of claim 8, wherein the disinfecting composition comprises hydrogen peroxide and peroxyacetic acid.

12. The disinfecting system of claim 8, wherein the atomizing device for producing the fog includes a piezo disc nebulizer operable at a frequency between about 1.50 MHz and about 2.50 MHz.

13. The disinfecting system of claim 8, further comprising:
a device for inducing an electrical charge in at least a portion of the liquid droplets.

14. A disinfecting apparatus comprising:
at least one rotary disc atomizer; and
a port for discharging an atomized disinfecting composition,
wherein the at least one rotary disc atomizer includes a multi-head high-speed rotary disc nebulizer operable to produce droplets of disinfecting composition having a diameter between about 2 microns and about 20 microns.

15. The disinfecting apparatus of claim 14, wherein the at least one rotary disc atomizer is operable to produce droplets of disinfecting composition having a diameter between about 2 microns and about 5 microns.

16. The disinfecting apparatus of claim 14, further comprising:
a tank for containing the disinfecting composition.

17. A disinfecting apparatus comprising:
at least one rotary disc atomizer;
a port for discharging an atomized disinfecting composition;
a dehumidifying device; and
at least one filter having low-micron moisture droplet air-flow vanes.

18. The disinfecting apparatus of claim 17, wherein the at least one filter includes an impingement-type separator.

* * * * *